United States Patent [19]

Oka et al.

[11] Patent Number: 4,654,444
[45] Date of Patent: Mar. 31, 1987

[54] FLUORINE-CONTAINING DIACYLPEROXIDES AND USE THEREOF

[75] Inventors: Masahiko Oka, Ohtsu; Shigeru Morita, Ikeda, both of Japan

[73] Assignee: Daikin Industries, Ltd., Osaka, Japan

[21] Appl. No.: 813,545

[22] Filed: Dec. 26, 1985

[30] Foreign Application Priority Data

Dec. 27, 1984 [JP] Japan .................................. 59-278997

[51] Int. Cl.$^4$ ............................................ C07C 179/16
[52] U.S. Cl. ...................................................... 568/560
[58] Field of Search ............................................ 568/560

[56] References Cited

U.S. PATENT DOCUMENTS 3,436,424 4/1969 Anderson ............................ 568/560

FOREIGN PATENT DOCUMENTS 1132412 10/1968 United Kingdom ................ 568/560

*Primary Examiner*—Werren B. Lone
*Attorney, Agent, or Firm*—Birch, Stewart, Kolasch & Birch

[57] ABSTRACT

A novel fluorine-containing diacylperoxide of the formula:

$$[RO\!-\!(CH_2CF_2CF_2O)_n\!-\!CH_2CF_2COO\!-\!]_2 \qquad (I)$$

wherein R is a $C_1$-$C_{10}$ hydrocarbon group or halogen-containing hydrocarbon group, and n is an integer of 0 to 3, which can initiate polymerization of an ethylenically unsaturated monomer at a relatively low temperature.

2 Claims, No Drawings

FLUORINE-CONTAINING DIACYLPEROXIDES AND USE THEREOF

FIELD OF THE INVENTION

The present invention relates to novel fluorine-containing diacylperoxides and use thereof, particularly as an polymerization initiator for ethylenically unsaturated monomers.

BACKGROUND OF THE INVENTION

Hitherto, many diacylperoxides have been synthesized and studied, and various diacylperoxides useful as initiators in the polymer industries are prepared and commercially available.

The peroxide to be used as a polymerization initiator for a fluorine-containing monomer is generally required to have following characteristics:

1. Since the fluorine-containing monomer usually has high reactivity, it is desirable to carry out their polymerization under milder condition, for example, at a low temperature. Accordingly, the peroxide is required to liberate an active radical at a low temperature.

2. Since radicals of propagating fluorine-containing polymeric chains generated during polymerization are active, the peroxide desirably hardly proceeds or does not proceed side reactions such as chain transfer reaction.

3. Peroxide residues bonded to the chain ends of the polymer molecules should be thermally stable.

As the peroxides which satisfy the above requirements, there are fluorine-containing diacylperoxides such as

However, these conventional fluorine-containing diacylperoxides are used at a polymerization temperature of 10° to 40° C. or higher to achieve a practical decomposition rate of the peroxide.

SUMMARY OF THE INVENTION

One object of the present invention is to provide novel fluorine-containing diacylperoxides which can liberate free radicals at a comparatively low temperature.

Another object of the present invention is to provide a polymer having a terminal group which is easily changed to a hydroxyl group to give a so-called telechelic polymer.

Accordingly, the present invention provides a novel fluorine-containing diacylperoxide of the formula:

wherein R is a $C_1$–$C_{10}$ hydrocarbon group or halogen-containing hydrocarbon group, and n is an integer of 0 to 3.

The present invention also relates to the use of the fluorine-containing diacylperoxide (I) as a polymerization initiator for an ethylenically unsaturated monomer.

DETAILED DESCRIPTION OF THE INVENTION

The fluorine-containing diacylperoxide (I) of the invention easily liberates a radical at a low temperature and effectively initiates the polymerization of the monomer. Surprisingly, to the polymer prepared by the use of the diacylperoxide (I) as the polymerization initiator, hydroxyl groups can be introduced at the polymer chain ends to give a telechelic polymer. Although many attempts have been made to produce telechelic polymers by the use of various polymerization initiators, a telechelic polymer having terminal hydroxyl groups has not been prepared.

In the fluorine-containing diacylperoxide (I), R is usually a $C_1$–$C_{10}$ hydrocarbon group or halogen-containing hydrocarbon group and includes a saturated or unsaturated, substituted or unsubstituted, aliphatic or aromatic group. The substituent may be a lower alkyl group, a phenyl group and the like. Specific examples of the group R are methyl, ethyl, isomeric propyl, isomeric butyl, pentyl, allyl, phenyl, methylphenyl, triphenylmethyl, chloroethyl, chloropropyl, 2,2,3,3-tetrafluoropropyl, 2,2,2-trifluoroethyl, and the like.

Specific examples of the fluorine-containing diacylperoxide (I) are as follows:

 (Ia)

 (Ib)

 (Ic)

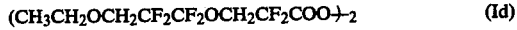 (Id)

 (Ie)

 (If)

 (Ig)

 (Ih)

The novel fluorine-containing diacylperoxide (I) may be prepared by reacting an acyl halide of the formula:

 (II)

wherein R and n are the same as defined above and X is halogen such as fluorine, chlorine, bromine and iodine, with $Na_2O_2$ in water and extracting the product with a suitable solvent. The solvent used is one insoluble in water. A fluorine-containing solvent (e.g. trichlorotrifluorethane, tetrachlorodifluoroethane, trichlorofluoromethane and the like) is preferably used, although a water-insoluble hydrocarbon type solvent (e.g. benzene, toluene, xylene, hexane, heptane, and the like) can be used. The reaction temperature is usually −20° to 0° C.

The fluorine-containing diacylperoxide (I) of the invention is useful as an initiator for polymerizing various ethylenically unsaturated monomers. Specific examples of the monomers are hydrocarbon monomers (e.g. ethylene, propylene, vinyl chloride, vinylidene chloride, vinyl acetate, vinyl butyrate, acrylic acid, methacrylic acid, acrylate or methacrylate such as methyl acrylate or methacrylate, acrylamide, methacrylamide, acrylonitrile, acrolein, methyl vinyl ketone, methyl vinyl ether, ethyl vinyl ether, diethyl fumarate, styrene and the like) and fluorocarbon monomers (e.g. vinyl fluoride, vinylidene fluoride, trifluoroethylene, tetrafluoroethylene, chlorotrifluoroethylene, hexafluoropropene, per(fluoroalkyl vinyl ether) and the like). The monomer may be used alone or a mixture with at least one of other monomers.

The polymerization of the ethylenically unsaturated monomer using the fluorine-containing diacylperoxide (I) of the invention as the initiator may be carried out under substantially the same condition as in a conventional polymerization of the monomer. The polymerization is usually initiated at a temperature of $-10°$ to $+30°$ C. and preferably carried out in a solvent. The solvent may be the same as those used in the conventional method. Particularly for polymerization of fluorohydrocarbon monomers, used is a fluorine-containing solvent which hardly suffers from chain transfer such as perfluorokerosene, octafluorodichlorobutane, 1,1,2-trifluoro-1,2,2-trichloroethane, 1,2-difluoro-1,1,2,2-tetrafluoroethane and the like.

The fluorine-containing diacylperoxide (I) of the invention has a terminal ether group in the molecule, which is also contained as a terminal group in the polymer produced by the use of the diacylperoxide (I). The terminal ether group in the polymer is easily changed to the hydroxyl group by thermal treatment or acid treatment with an inorganic acid (e.g. hydrochloric acid, hydrobromic acid and the like) or an organic acid (e.g. trifluoroacetic acid and the like). Since the fluorine-containing diacylperoxide (I) of the invention contains fluorine atoms and can be decomposed at a comparatively low polymerization temperature as described above, the monomer is polymerized under comparatively mild conditions. Since it has a high activity, particularly for the fluorine-containing monomers, it can very effectively initiate the radical polymerization of said monomers. This is confirmed from the fact that the fluorine-containing diacyl peroxide (I) has a shorter half-life than the conventional peroxides.

The present invention will be hereinafter explained further in detail by following examples.

EXAMPLE 1

Production of [$(CH_3)_3COCH_2CF_2COO$]$_2$ (Ie)

To a solution of sodium chloride (10 g) in water (40 g) contained in a flask equipped with a stirrer cooled to $-20°$ C., $Na_2O_2$ (1.0 g) was added and then $\alpha,\alpha$-difluoro-$\beta$-t-butoxypropionyl chloride (B.P. 52°-53° C./30 mmHg) (5.0 g) was dropwise added with stirring at the same temperature. After the addition of the chloride, the reaction mixture was stirred at the same temperature for 30 minutes and then 1,1,2-trichloro-1,2,2-trifluoroethane (5 ml) was added and stirred at the same temperature for 30 minutes. Thereafter, an organic layer (about 6 ml) containing the produced peroxide was recovered. Iodometric titration of the organic layer revealed that the concentration of the entitled peroxide was about 0.3 g/ml.

EXAMPLE 2

In the same manner as in Example 1 but using 5 time amount of each reagent, the same procedures were repeated to obtain a solution (30 ml) containing the peroxide (Ie) in a concentration of 0.29 g/ml.

EXAMPLE 3

The solution containing the peroxide (Ie) prepared in Example 2 (1 ml) was diluted with 1,1,2-trichloro-1,2,2-trifluoroethane (9 ml) and kept on a water bath at 20° C. in a nitrogen atmosphere to decompose the peroxide (Ie). The half-life at 20° C. was about 21 minutes. The half-life of the peroxide (Ie) measured at 10° C. was about 108 minutes.

The activation energy of decomposition was calculated to be about 24.2 Kcal/mol.

For comparison, half-lives of the conventional peroxides at 20° C. are as follows:
DLP—385 minutes
DHP—360 minutes
DIP—1,066 minutes.

EXAMPLE 4

In a stainless steel made reactor, vinylidene fluoride (17.1 g), perfluoropropene (19.2 g) and the solution of the peroxide (Ie) prepared in Example 2 (2 ml) were changed and retracted at 20° C. for 21 hours during which the interior pressure dropped from 22 $Kg/cm^2G$ to 20 $Kg/cm^2G$.

After the reaction, the unreacted monomers were distilled off to obtain a liquid polymer (3.5 g). The presence of t-butyl terminal groups was confirmed by NMR analysis.

The molar ratio of vinylidene fluoride and perfluoropropene was 77.3/22.7 according to IR and NMR analyses. The molecular weight was about 4,500 according to GPC.

EXAMPLE 5

Introduction of terminal hydroxyl groups to the polymer

A part of the polymer prepared in Example 4 was heated at 200° C. for 3 hours. IR and NMR analyses revealed that about 80% of the t-butyl terminal groups were converted to the hydroxyl groups while the rest of them remained unchanged.

EXAMPLE 6

Introduction of terminal hydroxyl groups to the polymer

A part of the polymer prepared in Example 4 was treated with trifluoroacetic acid overnight, washed with water and dried. IR and NMR analyses revealed that about 92% of the terminal t-butyl groups were converted to the hydroxyl groups.

EXAMPLE 7

Styrene monomer (2 ml) and the solution of the peroxide (Ie) prepared in Example 2 (1 ml) were charged in a glass ampoule, evacuated and reacted at a room temperature for 5 hours.

After the reaction, the content in the ampoule was poured in methanol to precipitate a polymer. The molecular weight of the polymer was 3,080 according to GPC.

The polymer was treated in the same manner as in Example 6 to give polystyrene having the hydroxyl groups at the polymer chain ends, which was confirmed by NMR analysis.

What is claimed is:

1. A fluorine-containing diacylperoxide of the formula:

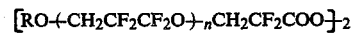     (I)

wherein R is a $C_1$-$C_{10}$ hydrocarbon group or halogen-containing hydrocarbon group, and n is an integer of 0 to 3.

2. A fluorine-containing diacylperoxide according to claim 1, wherein R is a group selected from the group consisting of methyl, ethyl, isomeric propyl, isomeric butyl, pentyl allyl, phenyl, methylphenyl, triphenylmethyl, chloroethyl, chloropropyl, 2,2,3,3-tetrafluoropropyl and 2,2,2-trifluoroethyl.

* * * * *